United States Patent
Mendoza et al.

(10) Patent No.: US 9,932,291 B2
(45) Date of Patent: Apr. 3, 2018

(54) REDUCED FOULING PROCESS FOR THE PRODUCTION OF METHYL METHACRYLATE

(71) Applicant: Rohm and Haas Company, Philadelphia, PA (US)

(72) Inventors: Joy L. Mendoza, Seabrook, TX (US); Philippe P. Maillot, Kingwood, TX (US); Mingyu Ye, Deer Park, TX (US); Stacy W. Hoy, IV, Houston, TX (US)

(73) Assignee: Rohm and Haas Company, Collegeville, PA (US)

( * ) Notice: Subject to any disclaimer, the term of this patent is extended or adjusted under 35 U.S.C. 154(b) by 0 days.

(21) Appl. No.: 15/521,440

(22) PCT Filed: Oct. 13, 2015

(86) PCT No.: PCT/US2015/055209
§ 371 (c)(1),
(2) Date: Apr. 24, 2017

(87) PCT Pub. No.: WO2016/069251
PCT Pub. Date: May 6, 2016

(65) Prior Publication Data
US 2017/0334827 A1    Nov. 23, 2017

Related U.S. Application Data

(60) Provisional application No. 62/068,991, filed on Oct. 27, 2014.

(51) Int. Cl.
*C07C 67/20*    (2006.01)
*C07C 69/54*    (2006.01)
*C07C 67/58*    (2006.01)
*C07C 67/54*    (2006.01)

(52) U.S. Cl.
CPC .............. *C07C 67/20* (2013.01); *C07C 67/54* (2013.01); *C07C 67/58* (2013.01); *C07C 69/54* (2013.01)

(58) Field of Classification Search
CPC .......... C07C 67/20; C07C 67/48; C07C 69/54
See application file for complete search history.

(56) References Cited

U.S. PATENT DOCUMENTS

| | | | |
|---|---|---|---|
| 2,472,487 A | 6/1949 | Lovell | |
| 3,006,950 A | 10/1961 | Francis et al. | |
| 3,821,286 A | 6/1974 | Pai et al. | |
| 5,403,963 A | 4/1995 | Adamski et al. | |
| 6,545,176 B1 | 4/2003 | Tsay et al. | |
| 7,253,307 B1 | 8/2007 | Carlson, Jr. et al. | |
| 2010/0069662 A1 | 3/2010 | Gropp et al. | |
| 2014/0051886 A1 | 2/2014 | Broell et al. | |

FOREIGN PATENT DOCUMENTS

| | | |
|---|---|---|
| CN | 1304357 C | 3/2007 |
| EP | 0561264 A2 | 9/1993 |
| EP | 0686623 A1 | 12/1995 |
| EP | 0999200 A1 * | 5/2000 |
| EP | 0999200 A1 | 5/2000 |

* cited by examiner

*Primary Examiner* — Paul A Zucker
(74) *Attorney, Agent, or Firm* — Edward L. Brant

(57) ABSTRACT

Fouling of an MMA process is reduced by acidifying a stream comprising recycled components.

9 Claims, 1 Drawing Sheet

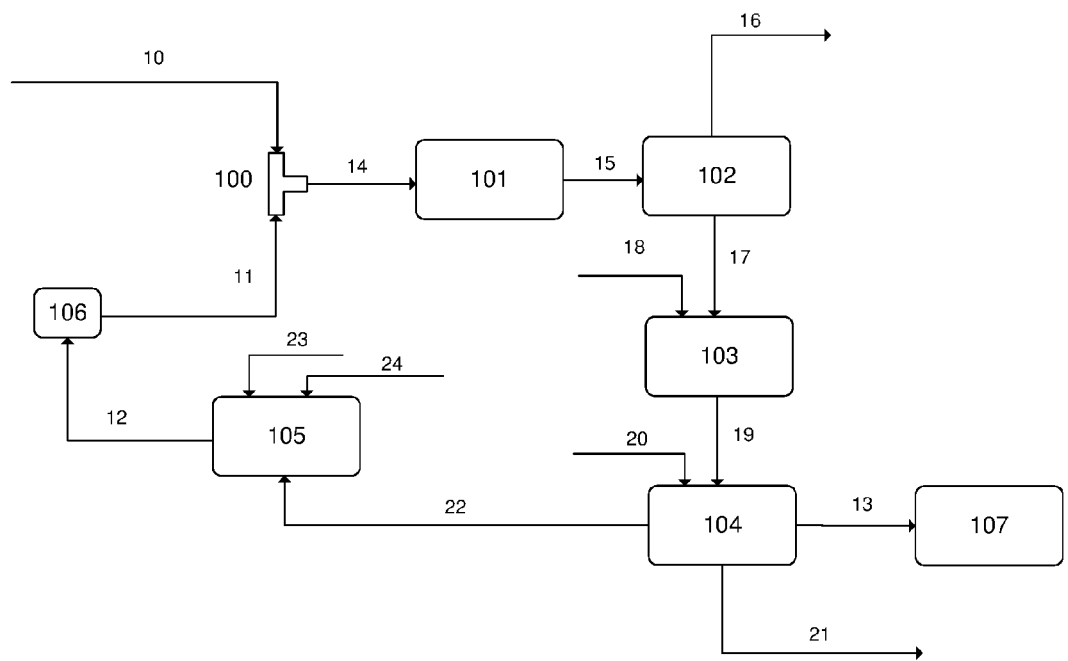

REDUCED FOULING PROCESS FOR THE PRODUCTION OF METHYL METHACRYLATE

BACKGROUND OF THE INVENTION

The invention relates to a process for producing methyl methacrylate (MMA).

MMA is a widely-produced industrial chemical that readily polymerizes. Typical end-use applications include: acrylic plastic sheeting; molding resins; polyvinyl chloride modifiers; processing aids; acrylic lacquers; floor polishes; sealants; auto transmission fluids; crankcase oil modifiers; automotive coatings; ion exchange resins; cement modifiers; water treatment polymers; electronic adhesives; metal coatings; and acrylic fibers. Methacrylate esters are especially prized in these applications and others because of the hardness they impart to the products in which they are used. The most popular industrial process for making MMA is the acetone cyanohydrin ("ACH") process. Methacrylate ester plants produce extremely large volumes of product; thus, any improvement in process yield, however slight, can have a significant positive economic impact.

In a conventional ACH process for the production of MMA, ACH is hydrolyzed in the presence of sulfuric acid to produce α-hydroxyisobutyramide ("HIBAM") and α-sulfatoisobutyramide ("SIBAM"). Next, the HIBAM and SIBAM are cracked to form methacrylamide (MAM) and by-products. The MAM is then esterified with methanol to produce the desired MMA product. The esterification product stream is a mixed product that is subjected to separation and purification steps to isolate the MMA product from the other compounds. Typically, a purified MMA product stream is produced, along with a purification residue comprising other compounds.

U.S. Pat. No. 7,253,307 prescribes the use of polymerization inhibitors to minimize polymer formation in a methyl methacrylate/methacrylic acid production process. The exhaustive list of inhibitors includes phenothiazine and its derivatives, hydroquinone and its derivatives, alkoxy-phenols, nitrosophenol and its salts, copper salts, and radical traps such as 4-hydroxy-2,2,6,6-tetramethyl-piperidinyloxy. The process relies on free-radical inhibitors present in the feed streams to the esterification reactor to prevent polymer formation in the reactor. These inhibitors are designed primarily to limit the concentration of free radicals and free radical polymerization, which leads to equipment fouling. However, despite the use of polymerization inhibitors, commercial MMA plants continue to face significant fouling issues.

In view of the shortcomings of the prior art, it would be desirable to have an improved process that would reduce unwanted polymerization in the production of MMA.

SUMMARY OF THE INVENTION

The process of the invention is such a process comprising: (a) contacting methacrylamide with methanol in an aqueous reaction medium in an esterification reaction zone in the presence of an acidic raw material to produce a first stream comprising MMA, water, methanol, the acidic raw material and MAA; (b) phase separating the first stream into a first aqueous stream comprising the acidic raw material, and a first organic liquid product stream comprising MMA, methanol and MAA; (c) neutralizing the MAA of the first organic liquid product stream with ammonia to produce a neutralized stream comprising MMA, methanol and ammonium methacrylate; (d) optionally adding water to the neutralized stream; (e) separating the neutralized stream into a second organic stream comprising MMA, and a second aqueous stream comprising methanol and ammonium methacrylate; (f) contacting the second aqueous stream with an acidifying agent to form an acidified aqueous stream; and (g) sending at least a portion of the acidified aqueous stream to the reaction zone.

Surprisingly, the acidification of step (f) is effective to reduce the formation of undesirable polymer in the process. Reduced polymer formation and accumulation allow longer production process run times, and reduce process downtime related to polymer removal.

BRIEF DESCRIPTION OF THE DRAWINGS

The FIGURE is a schematic process flow diagram for a process comprising one embodiment of the invention.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

As used herein, the terms "decanter," "phase separator," and "phase separation zone" are interchangeable, and refer to an apparatus, vessel, or device in which a multiphase input stream is allowed to separate into at least 2 phases such as, for example, a primarily organic phase and a primarily aqueous phase.

As used herein, the term "second aqueous stream" includes the aqueous stream withdrawn from the second phase separator as well as said stream after one or more other aqueous streams, other than the acidifying stream, have been added to it prior to the addition of the acidifying stream.

As used herein, the term "acidifying stream" means one or more streams comprising the acidifying agent in an amount to sufficiently lower the pH of the second aqueous stream.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The ACH process for the preparation of MMA comprises: (i) continuously feeding a first raw material comprising acetone cyanohydrin and an acidic raw material into a hydrolysis system; (ii) continuously hydrolyzing said first raw material in said hydrolysis system to form a hydrolysis product comprising SIBAM and HIBAM; (iii) continuously feeding said hydrolysis product to a cracking system; (iv) continuously cracking said hydrolysis product in said cracking system to form a cracking product, or "cracked mix" comprising methacrylamide (MAM) and the acidic raw material; (v) continuously feeding at least a portion of said cracking product and methanol to an esterification reactor; and (vi) continuously reacting said portion of said cracking product and said methanol in the esterification reactor to form MMA. The hydrolysis system may contain a single reactor or multiple reactors connected in series and may also employ one or more reactant addition points.

The acidic raw material serves as both a reactant and a solvent for the reaction. Preferred examples of the acidic raw material include sulfuric acid, oleum, and mixtures thereof. Using sulfuric acid at a concentration of greater than 95% is preferred, and a concentration of greater than 98% is more preferred.

The esterification reactor, in which the methyl methacrylate is produced, also produces by-product methacrylic acid. The methacrylic acid is recovered and recycled to the esterification reactor via a neutralization system, in which the methacrylic acid-containing organic phase is contacted with a base, such as ammonia, ammonium hydroxide, sodium hydroxide or any other suitable base, and the methacrylic acid is converted to a water-soluble salt, e.g., ammonium methacrylate. The resulting mixture is sent to a second phase separator, e.g., a decanter, in which organic and aqueous phases are separated into a second organic stream and a second aqueous stream. At least a portion of the ammonium methacrylate salt-containing aqueous phase is removed and recycled indirectly to the esterification reactor as the second aqueous stream.

The process of the invention improves the ACH process by reducing the amount of fouling. Fouling reduction is accomplished by reducing the amount of undesired polymer formed and/or accumulated. In one embodiment of the invention, the inventive process involves admixing an acidifying agent with the second aqueous stream, or a portion thereof, before it reaches step (a), i.e., before it reaches the esterification reaction zone. The second aqueous stream may be a stream resulting from adding other materials, such as other aqueous streams, to the second aqueous stream. The acidification of the second aqueous stream, which comprises methanol and ammonium methacrylate, prior to sending the stream to the esterification reaction zone surprisingly results in reduced polymer formation and, therefore, reduced polymer accumulation and fouling.

The amount of acidifying agent added to the second aqueous stream is an amount sufficient to reduce polymer formation. Polymer formation is measured in the first organic liquid product stream comprising MMA, methanol and MAA. Advantageously, the amount of acidifying agent admixed with the second aqueous stream before it reaches the esterification reaction zone is an amount sufficient to acidify the second aqueous stream before it reaches step (a) to a pH of less than 3, preferably less than 1.75, and more preferably less than or equal to 1.5. Various strong acids, such as strong mineral acids, advantageously can be employed as the acidifying agent to add to the second aqueous stream. Examples of preferred acids include sulfuric acid, oleum, and mixtures thereof. In one embodiment of the invention, another process stream can be employed as the source of the acidifying agent. For example, the cracked mix stream, which comprises the acidic raw material, can be employed as the acidifying agent.

The invention will be explained in more detail by reference to certain preferred embodiments and with reference to the drawings.

Referring now to the FIGURE, an acidifying agent, e.g., sulfuric acid, is fed via line 14 to static mixer 106, where it is mixed with aqueous recycle feed stream 12 from recycle feed tank 105. The acidifying agent can be fresh acid or can be acid taken from another process stream, such as the cracked mix stream 10 described hereinbelow. In one embodiment of the invention, the acidifying agent comprises a portion of cracked mix stream 10, which is diverted to mixer 106 via line 14. The effluent from mixer 106 is withdrawn via line 13. The amount of acidifying agent is sufficient to reduce the pH of aqueous recycle stream 12 to less than 3, i.e., the pH of stream 13 is less than 3. Stream 13 is heated in heater 107 and fed via line 11 to mixing tee 100. A 'cracked mix' comprising MAM, sulfuric acid, water and cracking by-products is fed via line 10 to the other inlet of tee 100. The effluent from tee 100 is sent via line 15 to esterification reaction zone 101. The esterification reaction zone effluent 16 comprises MMA, water, MAA, methanol, ammonium bisulfate and sulfuric acid, and is sent to a first phase separator, or decanter, 102 where it phase separates into a primarily organic crude MMA phase, or first organic liquid product stream 18, comprising MMA, methanol and MAA, and a primarily aqueous phase, or first aqueous stream 17, comprising a solution of sulfuric acid, ammonium bisulfate, and other components. The crude MMA phase is sent via line 18 to neutralization zone 103 where it is contacted with ammonia introduced via line 19. The neutralized organic phase, comprising MMA, methanol and ammonium methacrylate, is sent via line 20 to a second phase separation zone 104. Stream 21, the second organic stream, which comprises primarily MMA, is withdrawn from the second phase separation zone 104 and is sent for further purification. Stream 22, the second aqueous stream, comprising methanol and aqueous ammonium methacrylate, is sent to recycle tank 105, where it optionally is mixed with at least one other aqueous recycle stream 23. Fresh methanol is fed to recycle tank 105 via line 24. The aqueous phase from the first phase separator 102 is sent via line 17, the first aqueous stream, to a separation or purification zone.

Without being bound by any theory, it is believed that contacting the sulfuric acid acidifying agent with ammonium methacrylate, which is in stream 12 of the FIGURE, prior to esterification reaction zone 101 converts at least some of the ammonium methacrylate to MAA, and that this, via some mechanism that is not fully understood, reduces the amount of polymer formation.

A polymerization inhibitor can be employed in the process when the product and/or reactants comprise one or more polymerizable compounds. A wide variety of inhibitors are known and commercially available. The inhibitor may be added to the hydrolysis reactor alone or may be combined with another inhibitor and/or with a suitable solvent and then added to the process. Preferred solvents include, but are not limited to, acetone, ACH, trifluoroacetic acid, nitromethane, and/or sulfuric acid. Preferred solvents for use with phenothiazine inhibitors include one or more sulfur compounds. Such sulfur compounds include, but are not limited to, sulfuric acid, sulfur dioxide, methyl sulfone, tetramethylene sulfone ("sulfolane"), and dimethyl sulfoxide.

In various embodiments, the process of the invention may effectively reduce polymer formation by at least 50%, at least 60%, or at least 70%, compared to a process that is otherwise identical but which does not include the acidification of the second aqueous stream of the invention. Polymer formation is measured in the first organic liquid product stream comprising MMA, methanol and MAA.

SPECIFIC EMBODIMENTS OF THE INVENTION

The following examples are given to illustrate the invention and should not be construed as limiting its scope.

General Procedure

Esterification experiments are conducted in a Parr reactor to prepare MMA. A Parr Model #4563 bench top reactor with a 600 mL reactor cell volume, a heating mantle, an internal cooling loop and an internal impeller is paired with a Parr model #4848 reactor controller. All wetted parts are fabricated from zirconium alloy 702. The Parr reactor cell is charged with 269 grams of cracked mix comprising 58.4% sulfuric acid, 34.9% methacrylamide and 6.7% cracking by-products generated by cracking HIBAM and SIBAM. The reactor head is secured to the zirconium cell via bolts on the retaining collar. The assembled Parr reactor is placed in a reactor stand. The impeller is activated at 300 rpm. The reactor is then purged with nitrogen and is preheated to 138° C. A recycle feed vessel is charged with 231 grams of recycle feed comprising 45% water, 35% methanol, 5% MMA, and 15% ammonium methacrylate. The recycle feed vessel is pressurized to 80 psig with nitrogen and is heated to 60° C. At the start of the reaction, a valve separating the reactor and the feed vessel is opened and the recycle feed is injected into the reactor. During the reaction time, the pressure and temperature in the reactor are maintained at 80 psig and 138° C. After 30 minutes, the reaction is quenched by removing the heating mantle and passing cooling water through the internal cooling loop until the reactor contents are cooled to approximately 60° C. The reactor pressure is let down to atmospheric pressure and the cell is disassembled. The contents of the Parr reactor cell are liquid with two phases—organic and aqueous. The two-phase mixture in the Parr reactor cell is poured into a separatory funnel. The organic and aqueous phases are sampled and analyzed for soluble polymer.

Comparative Experiment A (Not an Embodiment of the Invention)

The General Procedure is repeated. The organic layer is sampled to measure soluble polymer. It is determined that the organic layer contains 1,796 ppmw of soluble polymer, as measured using organic-phase Gel Permeation Chromatography (GPC) using a poly-methylmethacrylate standard.

Example 1—Acidification with Sulfuric Acid

The procedure of Comparative Experiment A is repeated except that 250 grams of recycle feed is titrated with 30 grams of 99% sulfuric acid to adjust the pH from 6.3 to 1.5, and then 231 grams of this acidified recycle stream are placed in the recycle feed vessel. The organic layer contains 491 ppmw of soluble polymer, a 73% reduction relative to Comparative Experiment A.

Example 2—Acidification with a Process Stream

The procedure of Comparative Experiment A is repeated except that 250 grams of recycle feed is titrated with 31 grams of the cracked mix to adjust the pH from 6.3 to 1.5, and then 231 grams of this acidified recycle stream are placed in the recycle feed vessel. The organic layer contains 783 ppmw of soluble polymer, a 56% reduction relative to Comparative Experiment A.

These experiments demonstrate the unexpected reduction in polymer formation that may be achieved using the process of the invention.

What is claimed is:

1. A process for producing methyl methacrylate (MMA) comprising: (a) contacting methacrylamide with methanol in an aqueous reaction medium in an esterification reaction zone in the presence of an acidic raw material comprising sulfuric acid to produce a first stream comprising MMA, water, methanol, the acidic raw material and methacrylic acid (MAA); (b) phase separating the first stream into a first aqueous stream comprising the acidic raw material, and a first organic liquid product stream comprising MMA, methanol and MAA; (c) neutralizing the MAA of the first organic liquid product stream with ammonia to produce a neutralized stream comprising MMA, methanol and ammonium methacrylate; (d) optionally adding water to the neutralized stream; (e) separating the neutralized stream into a second organic stream comprising MMA, and a second aqueous stream comprising methanol and ammonium methacrylate; (f) contacting the second aqueous stream with an acidifying agent to form an acidified aqueous stream; and (g) sending at least a portion of the acidified aqueous stream to the reaction zone, wherein the amount of acidifying agent admixed with the second aqueous stream is an amount sufficient to acidify the second aqueous stream to a pH of less than 1.75 before it reaches the reaction zone.

2. The process of claim 1 wherein the separating of step (e) comprises at least one of distillation and phase separation.

3. The process of claim 1 wherein the separating of step (e) comprises phase separation.

4. The process of claim 1 wherein the acidifying agent comprises fresh acid or acid taken from another process stream.

5. The process of claim 4 wherein the acidifying agent comprises acid from another process stream.

6. The process of claim 4 wherein the acidifying agent comprises fresh acid.

7. The process of claim 1 wherein the contacting the second aqueous stream with an acidifying agent to form an acidified aqueous stream comprises admixing the acidifying agent with the second aqueous stream via a static mixer.

8. The process of claim 3 wherein the phase separation is conducted in a decanter, the acidic raw material comprises sulfuric acid, the acidifying agent comprises sulfuric acid, and the amount of acidifying agent is an amount sufficient to acidify the second aqueous stream to a pH of less than 1.75 before it reaches the reaction zone.

9. The process of claim 8 wherein the amount of acidifying agent is an amount sufficient to acidify the second aqueous stream to a pH of less than or equal to 1.5 before it reaches the reaction zone.

* * * * *